(12) United States Patent
Manley

(10) Patent No.: US 7,070,326 B2
(45) Date of Patent: *Jul. 4, 2006

(54) BARRIER AND CUSHIONING APPARATUS FOR DENTAL RADIOGRAPHY

(76) Inventor: Vonda Manley, 2725 Hidden Hills Way, Corona, CA (US) 92882

( * ) Notice: Subject to any disclaimer, the term of this patent is extended or adjusted under 35 U.S.C. 154(b) by 0 days.

This patent is subject to a terminal disclaimer.

(21) Appl. No.: 11/102,328

(22) Filed: Apr. 7, 2005

(65) Prior Publication Data

US 2005/0265522 A1 Dec. 1, 2005

Related U.S. Application Data

(63) Continuation-in-part of application No. 10/854,764, filed on May 26, 2004, now Pat. No. 7,004,627.

(60) Provisional application No. 60/529,190, filed on Dec. 12, 2003.

(51) Int. Cl.
*A61N 6/14* (2006.01)
(52) U.S. Cl. ...................... 378/168; 378/170
(58) Field of Classification Search ........ 378/168–170, 378/176, 191; 206/455
See application file for complete search history.

(56) References Cited

U.S. PATENT DOCUMENTS 6,811,312 B1 * 11/2004 Bratslavsky et al. ........ 378/191
2002/0181658 A1 * 12/2002 Garcia ........................ 378/169

* cited by examiner

Primary Examiner—David V. Bruce
Assistant Examiner—Hoon Song
(74) Attorney, Agent, or Firm—Birch, Stewart, Kolasch & Birch, LLP

(57) ABSTRACT

A barrier and cushioning apparatus for use with a digital dental x-ray detection sensor or conventional film packet. The apparatus provides an improved degree of comfort, protection and safety for a patient while at the same time avoiding contamination of the sensor. The barrier and cushioning apparatus may be configured in a number of different ways with or without adhesive positioning strips to accommodate various sensor holders, baskets, and other devices used in conjunction with the digital sensor. The barrier and cushioning apparatus may be configured in a number of different ways with bite tabs which allow the patient to hold the sensor or film and oral cushion in place by occluding on the bite tab.

15 Claims, 16 Drawing Sheets

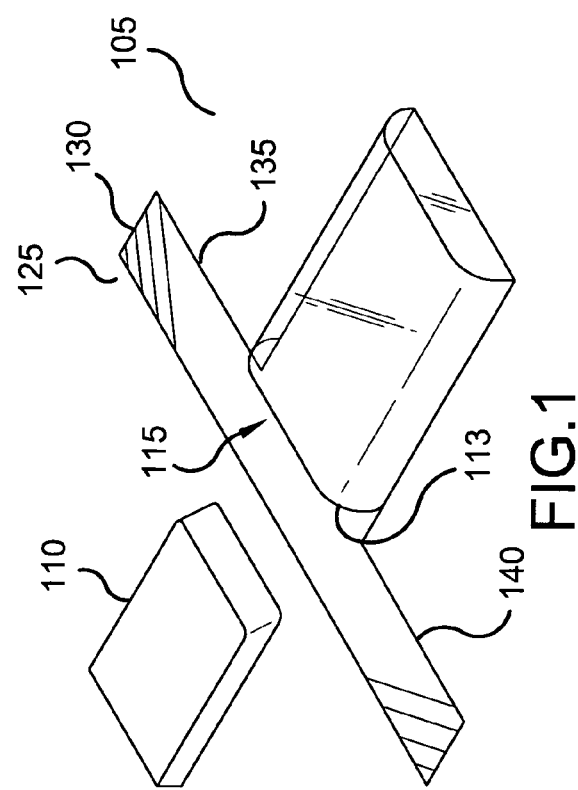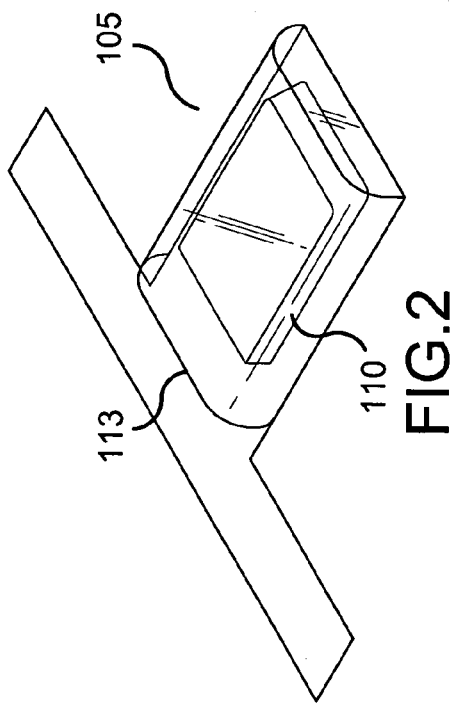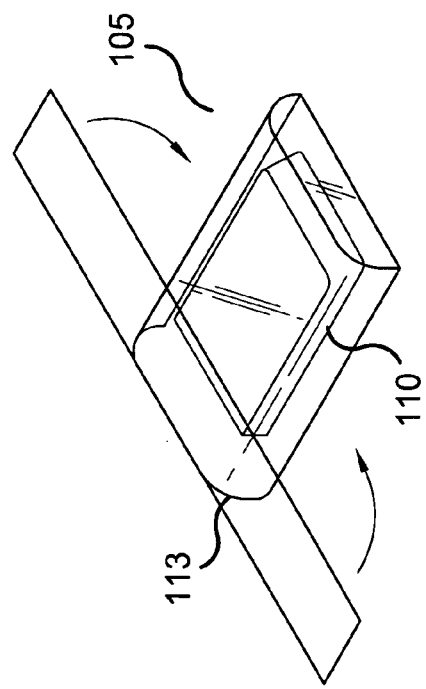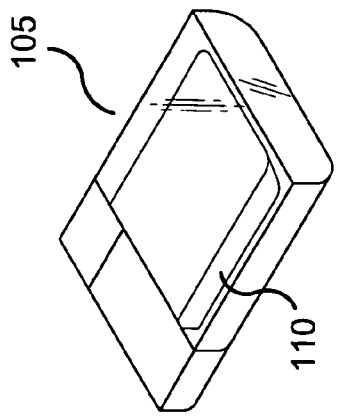

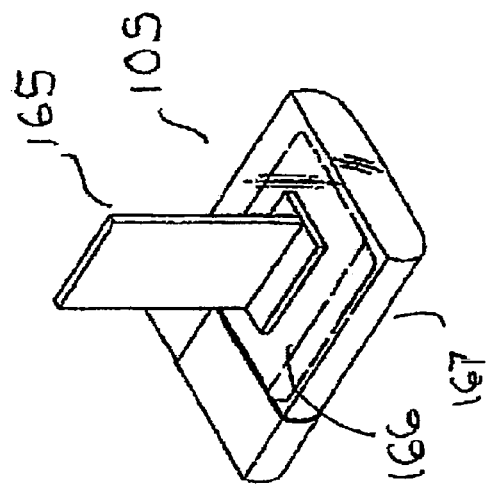
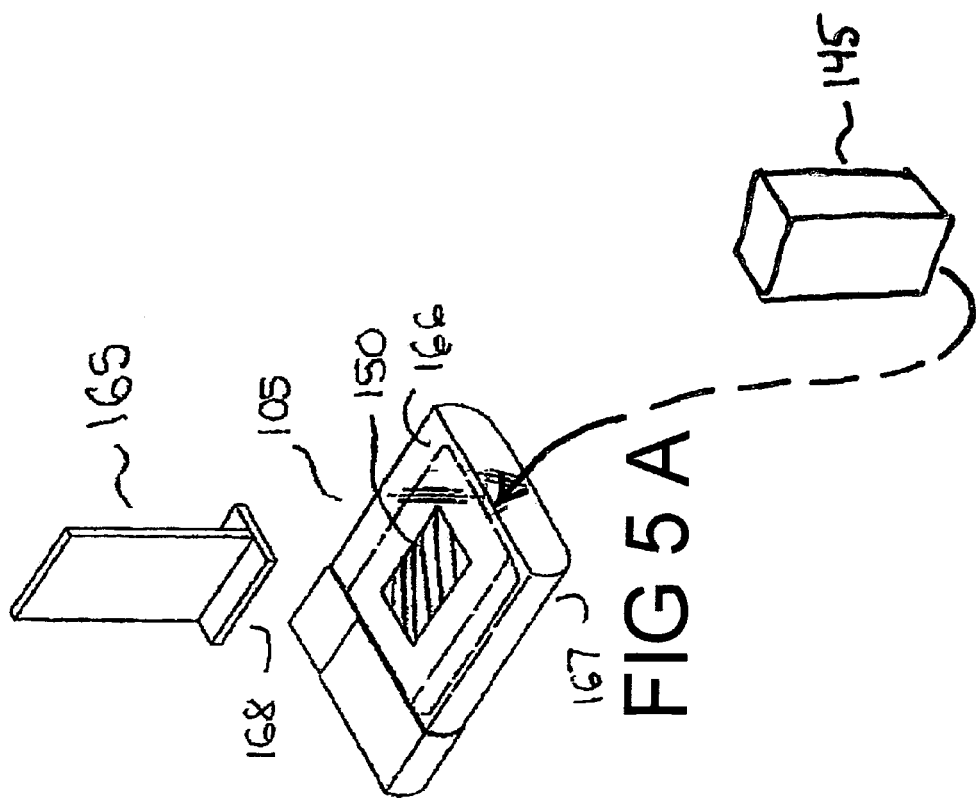

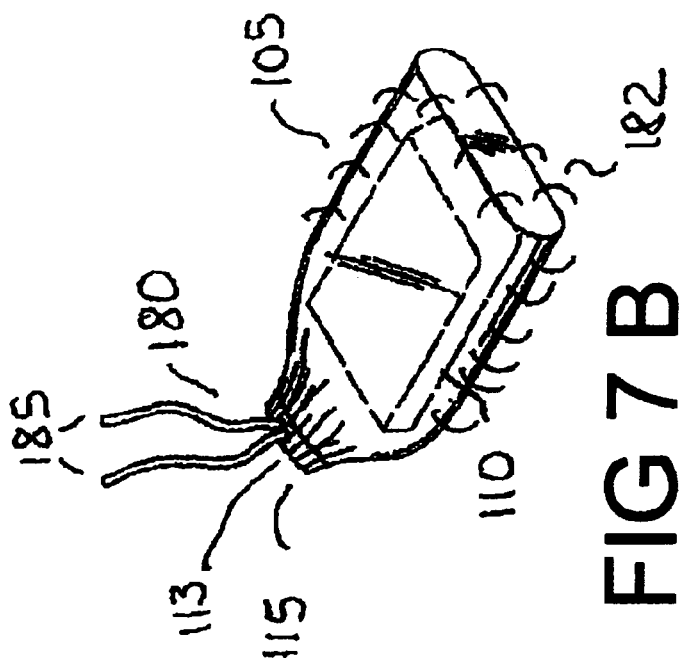
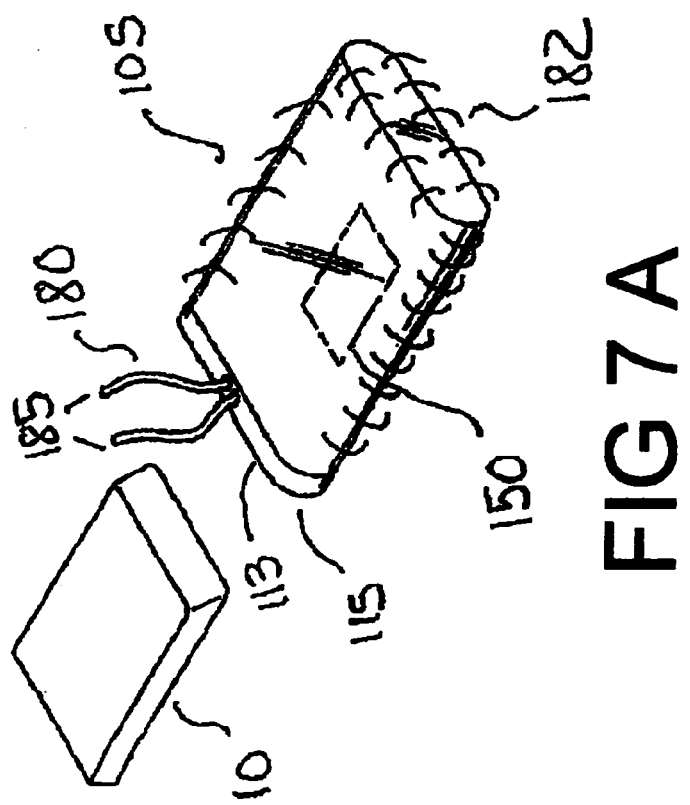

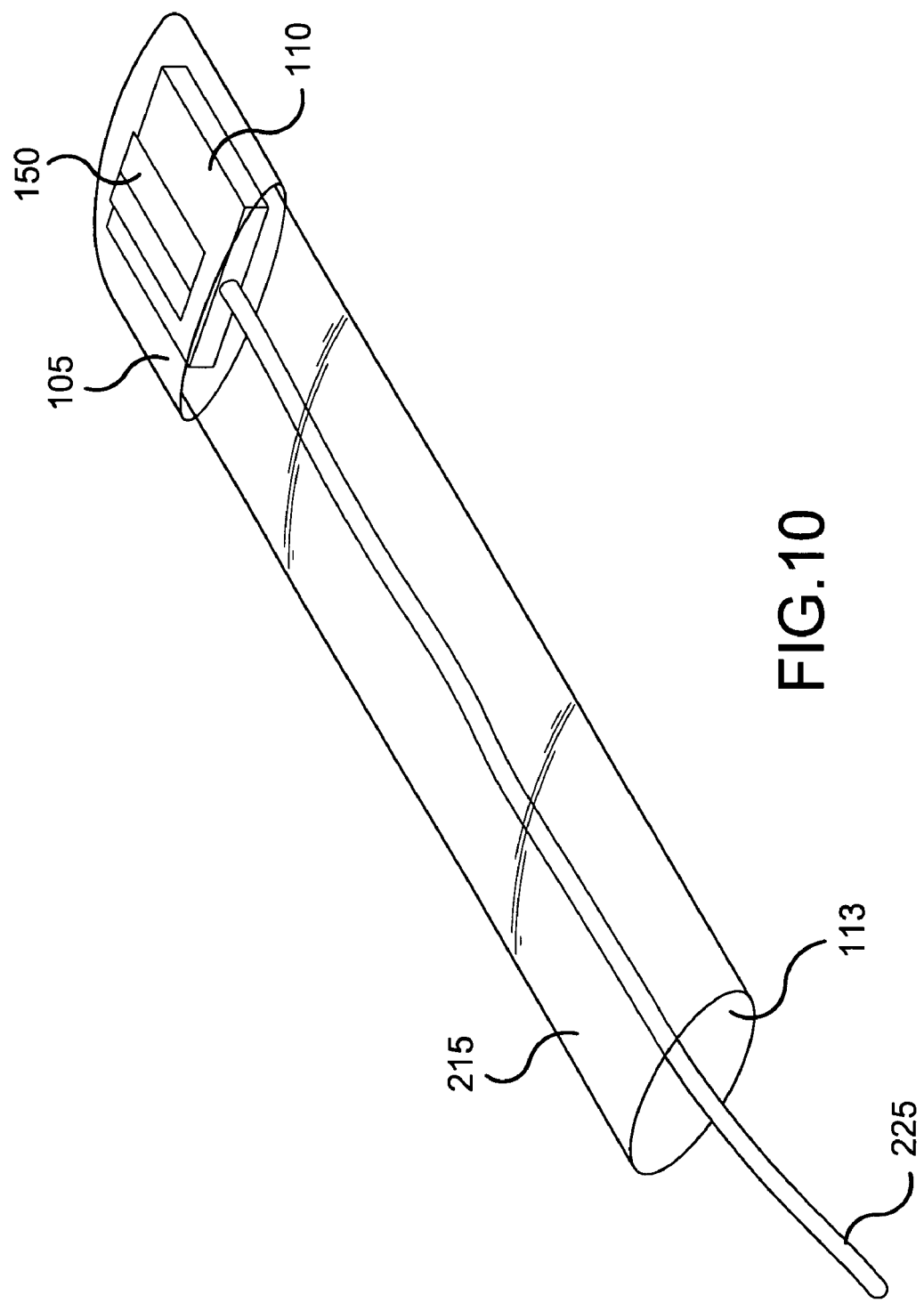

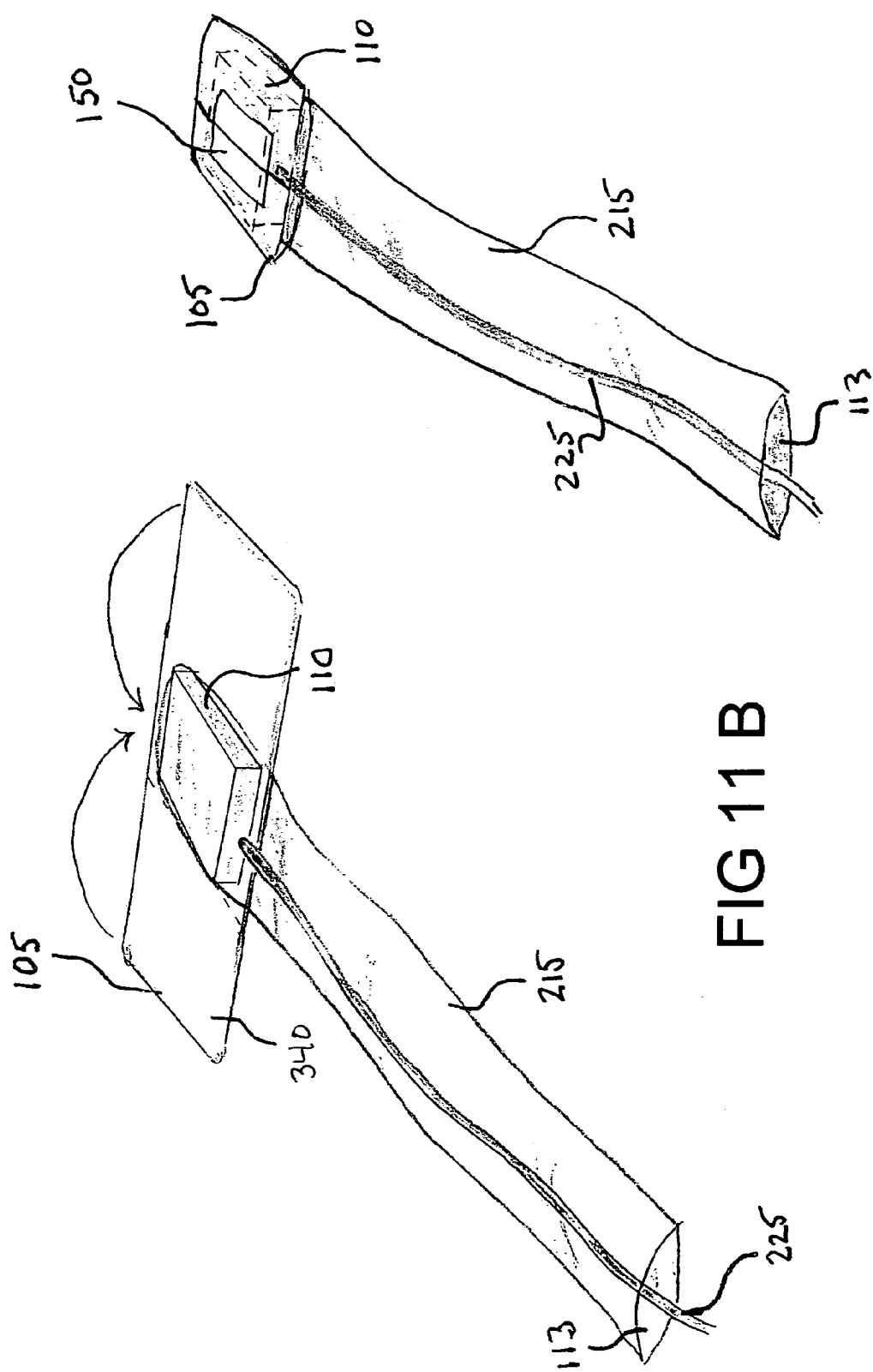

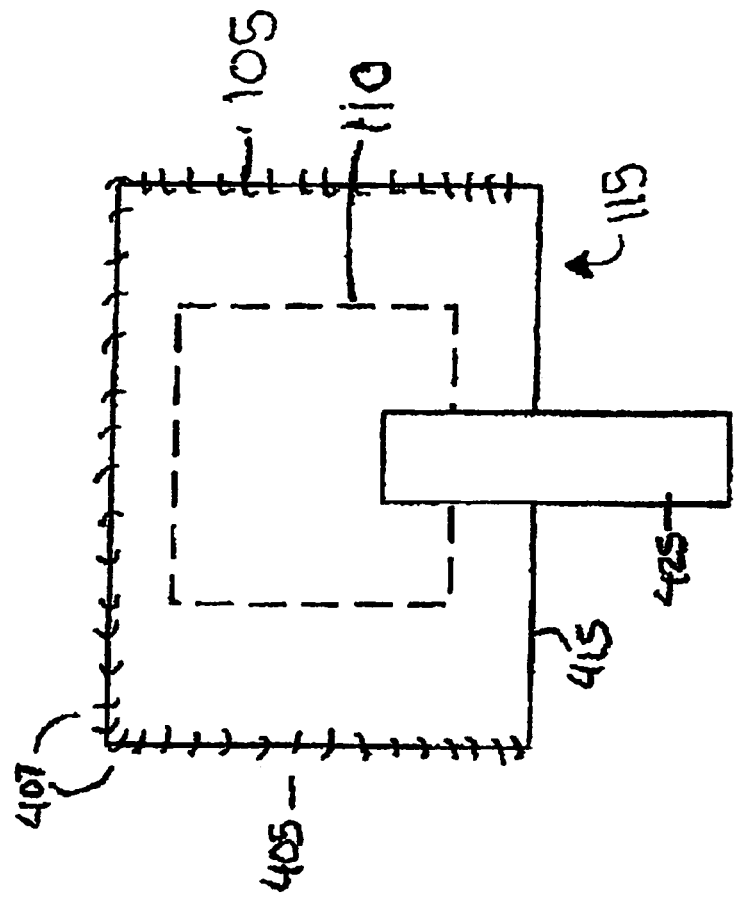
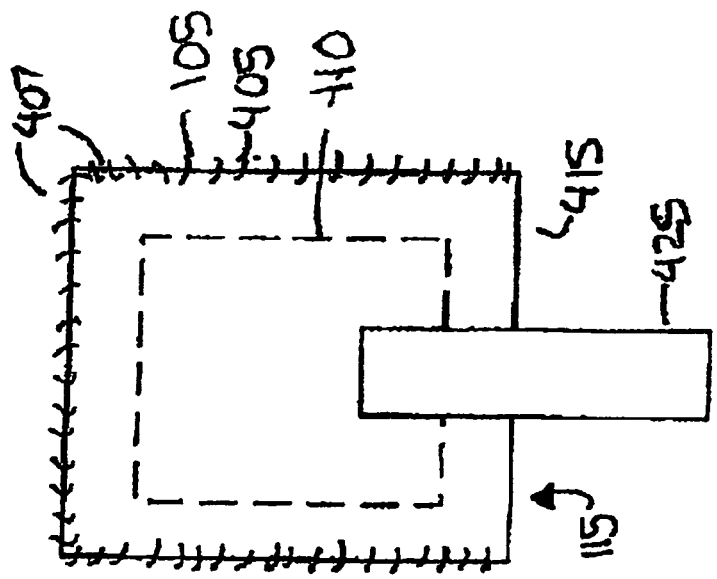
FIG 13 B
FIG 13 A

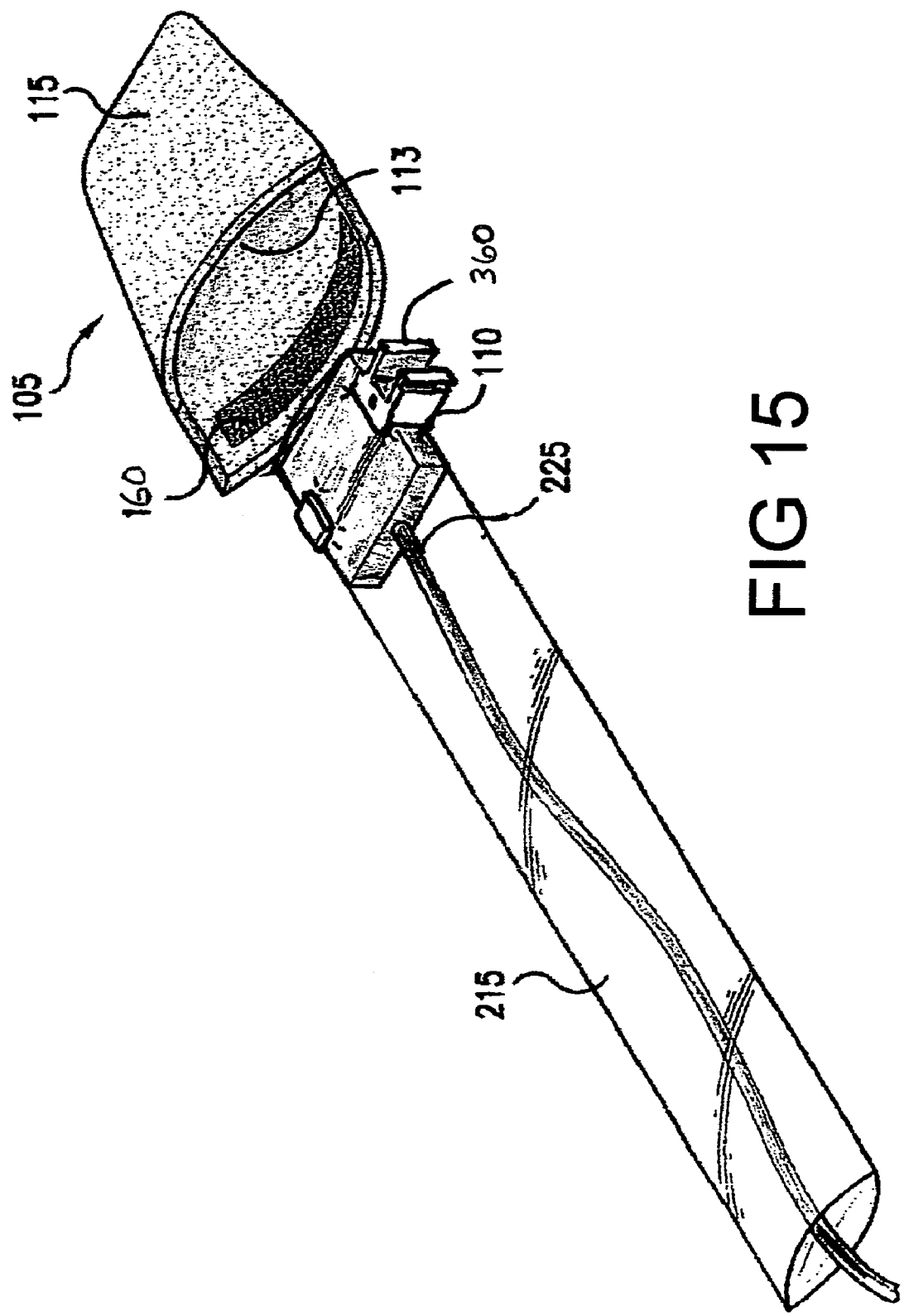

BARRIER AND CUSHIONING APPARATUS FOR DENTAL RADIOGRAPHY

This application is a continuation-in-part application and claims the benefit of U.S. application Ser. No. 10/854,764, filed on May 26, 2004, now U.S. Pat. No. 7,004,627 and U.S. Provisional Application No. 60/529,190, filed on Dec. 12, 2003, both entitled BARRIER AND CUSHIONING APPARATUS FOR DENTAL RADIOGRAPHY. The entire disclosure of the prior applications is considered a part of the disclosure of the accompanying application and is hereby incorporated by reference therein.

BACKGROUND

1. Field of the Invention

The present teachings relate to the field of dental radiography, and more particularly to an intraoral barrier for digital radiographic sensor devices. The present invention particularly relates to a digital radiographic sensor device that is comfortable for a patient and easy to use for a dental professional.

2. Description of the Related Art

Digital radiographic sensor systems are increasingly used in the dental field as an alternative to conventional film-based acquisition systems. Digital radiographic imaging provides a number of potential benefits including: reduced processing times with rapid imaging results, elimination of film developer chemicals and mounting requirements and the ability to conveniently perform a number of specialized functions using the resultant digital radiographs including; calibrated length measurement, image enhancement, digital zooming, colorizing, archiving, etc.

Unfortunately, digital radiographic sensors are subject to a number of usage considerations that should be addressed to improve patient comfort and minimize the potential for contamination of the sensor. For example, most dental sensors are not designed to permit autoclaving or sterilization between uses and their cost preclude one-time disposable use. As a consequence, a contamination risk exists as the same device is typically intended to be shared between numerous patients. To address this problem, dental sensors may be used in conjunction with a protective barrier, which serves to shield the device from a patient's saliva and prevent cross contamination between patients.

Conventional protective barriers are generally formed from a plastic sheath or enclosure which surrounds the dental sensor and may be removed and disposed of after use. One problem with such barriers is that they may be formed so as to have a seam or edge which may engage or rub against the patient's oral tissues creating discomfort during the imaging process. A further problem with such conventional barriers is that they may be cumbersome to use and/or provide inadequate protection against contamination.

Typically, dental sensors such as those described above are secured to a holder or bite plate during use. The holder or bite plate also possesses potentially hard, rough or sharp edges and may likewise cause patient discomfort during use. Properly securing the dental sensor to the holder or bite plate may be additionally complicated by the use of the protective barrier which may encourage slippage between these components.

From the foregoing, it will be appreciated that there is a need for an improved protective barrier design to be used in connection with digital sensors to increase patient comfort and alleviate potential tissue injury during imaging. Additionally, there is a need to reduce patient discomfort arising from the holder or bite plate used in connection with the digital sensor.

SUMMARY

The aforementioned needs are satisfied by an oral cushioning barrier that improves patient comfort during radiographic imaging while reducing the risk of tissue injury resulting from insertion of a radiographic detection device within a patient's oral cavity. The oral cushion may be formed in a number of different sizes and configurations and adapted for use with conventional x-ray film packets, as well as, newer digital x-ray sensors. The oral cushion incorporates an integrated adhesive section that may be used to secure various positioning accessories to the cushion so as to facilitate alignment of the radiographic detection device during use. The oral cushion may also be configured to provide a generally soft barrier about at least a portion of the positioning accessory further improving patient comfort and reducing the risk of tissue injury. The oral cushion may further be configured to substantially enclose the radiographic detection device thereby reducing the risk of contamination of the device.

In various embodiments, the oral cushion comprises a foam or plastic sheath formed to substantially enclose the radiographic detection device within a cushioning region provided to be positioned about the radiographic detection device and various portions of an associated positioning accessory in regions that may potentially engage with the oral tissue of the patient. Additionally, the oral cushion may be generally constructed in such a manner so as to reduce undesirable bulk that might otherwise hinder placement of the sensor within a holder, bite plate or within the patient's mouth directly.

In one aspect, the present teachings provide an intra-oral dental comfort device capable of being configured for use with a positioning accessory, the device comprising an oral cushion having first and second sides with a pocket disposed therebetween, the pocket dimensioned to receive and maintain a dental sensor in a generally secure position within the oral cushion, the oral cushion further configured to provide a comfort barrier between at least a portion of the dental sensor and tissue in a patient's oral cavity; and an adherent member disposed along at least a portion of the oral cushion, the adherent member configured to receive and secure the positioning accessory to the oral cushion such that the dental sensor may be positioned in a desired orientation within the patient's oral cavity allowing imaging of at least a portion of the patient's teeth by an imaging device used in connection with the dental sensor.

In another aspect, the present teachings provide a method for improving the comfort characteristics of a dental sensor to be used during x-ray acquisition. The method comprising the steps of enclosing at least a portion of the dental sensor with an oral cushion, the oral cushion configured to receive the dental sensor in a pocket region of the oral cushion whereby the dental sensor is retained in a generally secure position within the oral cushion; securing a positioning accessory to the oral cushion using an adherent member disposed along at least a portion of the oral cushion such that the dental sensor may be positioned in a desired orientation within the patient's oral cavity; and positioning a comfort strip extending from the oral cushion along at least a portion of the positioning accessory, the comfort strip creating a generally soft boundary between at least a portion of the sensor positioning accessory and the patient's oral cavity.

BRIEF DESCRIPTION OF THE DRAWINGS

FIG. 1 illustrates one embodiment of an oral cushion for use with a digital radiographic sensor or x-ray film packet.

FIGS. 2–4 illustrate a mode for enclosing a wireless sensor or film packet within the oral cushion.

FIGS. 5–6 illustrate an integrated adhesive portion formed on the oral cushion that may be used to secure the sensor to an oral alignment or positioning device.

FIGS. 7A–7B illustrates another embodiment of an oral cushion that incorporates a drawstring securing mechanism for containment of the sensor within the oral cushion.

FIG. 10 illustrates an embodiment of an oral cushion formed as a combination polybag with foam or cushioning material surrounding the polybag at the opposing end from the opening.

FIGS. 11A–B illustrate another configuration of an oral cushion or cushioning barrier to be used with various-oral alignment or positioning devices

FIGS. 13A–B illustrates further configurations of an oral cushion having a cushioning extension extending therefrom.

FIGS. 15 and 16 illustrate a further embodiment of an oral cushion that incorporates an elongated section designed to receive and contain a wired or wireless sensor.

DETAILED DESCRIPTION OF THE CERTAIN EMBODIMENTS

Figure 8B:
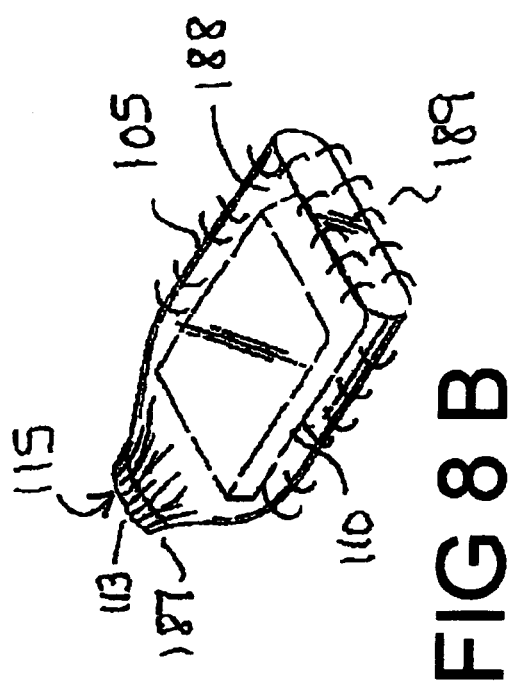
FIGS. 8A–8B illustrate a further embodiment of an oral cushion that incorporates an elastic securing mechanism for containment of the sensor within the oral cushion.

FIG. 1 illustrates one embodiment of an oral cushion 105 for use with a radiographic detection device or sensor 110. The sensor 110 comprises a component such as a digital radiographic sensor or conventional x-ray film packet configured to be inserted into a patient's oral cavity. The sensor 110 may further comprise a digital detection device of a wired or wireless variety. Like conventional x-ray film, these devices may be used in oral imaging applications. Examples of digital detection devices include computed dental radiography devices (CDRs) such as those produced by Schick Technologies (Long Island City, N.Y.). It will be appreciated that the illustrated sensor 110 represents but one of many possible sensor configurations and, as such, the oral cushion may be adapted for use with a variety of other sensor configurations without departing from the scope of the present teachings. In each of the various embodiments, the foam or adhesive may be printed with company names to permit private labeling or with instructions for use.

The oral cushion 105 comprises a pocket portion 115 generally conforming to the shape and dimensions of the sensor 110 with an opening 113 into which the sensor 110 may be positioned within the pocket 115. The cushioning barrier 105 may further comprise a flap section 125 formed to be folded in such a manner so as to substantially enclose the sensor 110 when inserted into the pocket 115. Enclosing the sensor 110 within the oral cushioning barrier 105 desirably reduces the risk of contamination of the sensor 110 and further provides significant cushioning coverage about the entirety of the sensor 110 as will be described in greater detail hereinbelow.

The flap section 125 of the sensor 110 may conform to various configurations and include an adhesive portion 130 that secures the flap section 125 in a desired position about the oral cushion 105 at least partially enclosing and securing the sensor 110 within the pocket 115. In one aspect, the flap section 125 comprises first and second wing sections 135, 140 joined to the pocket 115. When enclosing the sensor 110, a top portion of the oral cushion 105 may be folded to cover the opening 113 in the pocket 115 with the first and second wing sections 135, 140 further used to secure the top portion in a fixed position. Additional details of the sensor enclosing approach are discussed below in connection with FIGS. 2–4.

In various embodiments, the oral cushion 105 may be fabricated from a generally thin plastic or foam material capable of being folded and secured in the aforementioned manner. In one aspect, forming the oral cushion 105 in part or whole from foam or similar material desirably imparts a soft, supple, and/or comfort quality to the oral cushion 105. This feature desirably improves patient comfort when the sensor 110 is placed within the oral cavity by substantially reducing or eliminating tissue contact with sharp, rough or uncomfortable portions of the sensor 110 or associated positioning accessory that the patient might otherwise feel. Additionally, the oral cushion provides a generally soft layer between the oral tissue of the patient and the generally hard surface of the sensor 110 itself. In another aspect, the material used to form the oral cushion 105 may be scented, unscented, flavored or unflavored in order to enhance the patient's overall experience. In particular, it is envisioned that allowing the patient to select a particular scented or flavored oral cushion 105 would make the procedure more enjoyable for the patient and would especially help to alleviate the fear of younger patients.

In another aspect, the materials used to form the oral cushion 105 may be of different colors to allow the practitioner to differentiate between oral cushions 105 used in the anterior of the patient's mouth versus those used in the posterior of the patient's mouth. For example, blue colored oral cushions 105 may be used for the anterior sections of the patient's mouth and yellow colored oral cushions 105 may be used for the posterior sections of the patient's mouth. Color-coded cushions provide for ease of use and minimize the risk of confusion. Alternatively, different color-coded oral cushions 105 may be used to distinguish between oral cushions 105 used on the left side of a patient's mouth versus those used on the right side of a patient's mouth.

Typically, the oral cushion 105 may be constructed using relatively inexpensive manufacturing processes such that the cost per cushion 105 is generally kept low. Furthermore, the barrier 105 may be used as a disposable component in the imaging process wherein the sensor 110 used in connection with the cushion 105 does not necessarily require cleaning or sterilization between uses from one patient to the next. Providing a mechanism for enclosing the sensor 110 in this manner reduces or alleviates potential contamination of the sensor 110 by patient saliva and transmission of germs, dirt, bacteria, and other undesirable components. As will be appreciated by one of skill in the art, the oral cushion 105 of the present teachings further provides improved containment and securing of the sensor 110 as compared to conventional barriers and may improve patient comfort through the use of the foam or cushioning material. In another aspect designed to minimize the transmission of germs, the foam or soft material with which the oral cushion 105 is made, may be impregnated with an anti-bacterial or anti-microbial film.

FIGS. 2–4 illustrate another mode for enclosing the sensor 110 within the oral cushion 105. The sensor 110 is first inserted into the pocket 115 (see FIG. 2) through the opening 113. At this point the sensor 110 is partially enclosed within the pocket 115 and capable of being fully enclosed when the opening 113 is closed. To accomplish this, the top portion of the oral cushion 105 may be configured to cover the opening 113 by folding at least a portion of the top portion of the oral cushion 105 to substantially enclose the sensor 110 within the oral cushion 105 (see FIG. 3). In one aspect, the top portion of the oral cushion 105 is folded against the opening 113 positioning the first and second wing sections 135, 140 in proximity to the pocket 115. Thereafter, the first and second wing sections 135, 140 may be folded about the pocket 115, for example along the sides of the pocket, (see FIGS. 3–4) and secured in position by the adhesive portion 130. The result of these operations at least partially seal the opening 113 and substantially enclose at least a portion of the sensor 110 thereby forming a barrier layer about the sensor 110 and preventing direct contact of the sensor 110 with external contaminants, fluids, or saliva. In the case of a wireless dental sensor, the aforementioned enclosure approach may desirably seal substantially all portions of the wireless dental sensor within the oral cushion 105 providing an effective barrier against contamination and a generally soft guard to patient tissue. Another embodiment has the oral cushion 105 shaped like an envelope with a single fold-over closing flap. A film, wireless sensor or wire equipped sensor 110 may be enclosed. In order to ensure complete protection from germs, saliva, etc., a plastic barrier or polybag may be used, to place the film, or sensor into, prior to placing it in the oral cushion 105. A retraction device may or may not be used as an additional safety measure to prevent accidental aspiration. An adhesive strip, 150, may be placed in any number of configurations on the external portion of the oral cushion 105 for ease in attachment to positioning devices.

FIGS. 5A, B,–6 illustrate an integral adhesive positioning strip 150 formed about the oral cushion 105. The adhesive positioning strip 150 may be used to secure the oral cushion 105 (and at least partially enclosed sensor 160) to an oral alignment or positioning accessory such as depicted at 5B 145 or 5A–6, 165. In one aspect, the adhesive positioning strip 150 comprises a section of double-sided adhesive tape, foam, or the like which may be secured to a portion of the oral cushion 105 on one side and to the oral alignment or positioning device, 145 or 165 on the other side (see FIG. 6). The positioning accessory may comprise a number of different accessories typically used for sensor positioning including, by way of example, a bite tab 145, a bite plate 165, an endodontic tab, an anterior periapical tab, a bitewing tab, a posterior periapical holder, or other such accessories that are configured to be secured to the sensor 110 with a desired alignment.

The adhesive positioning strip 150 may be located on the oral cushion 105 in a variety of different locations to accommodate various configurations of oral alignment or positioning devices 145, 165. For example, in one aspect, the adhesive positioning strip 150 may be centrally positioned along a front or back surface 166, 167 facilitating proper positioning of the positioning device 165 with respect to the sensor 110. The size of the adhesive positioning strip 150 may further be configured to generally conform to a contact area 168 of the positioning device 165 that will be in contact with the oral cushion 105. While the embodiments shown in FIGS. 5A–6 illustrate the adhesive positioning strip 150 as being located on the back surface 166 of the cushion 105 it will be appreciated that the adhesive positioning strip 150 may be positioned as necessary about the cushion to accommodate various configurations of positioning devices. For example, separate adhesive positioning strips 150 may be positioned along the front and back surfaces 166, 167 to give the user a choice of locations to secure the positioning device 145, 165. Additionally, the adhesive positioning strip 150 may be oriented along one or more sides of the cushion 105 depending on the configuration of the positioning device 145, 165.

In various embodiments, the adhesive positioning strip 150 may further comprise a removable liner or peel-off portion that covers and protects the adhesive portion prior to use. In one aspect, the liner comprises a paper or plastic layer (possibly treated with an anti-stick coating) that may be easily removed from the adhesive portion and allows the cushions 105 to be stored or stacked together without adherence to each other. In various embodiments, the liner is of a commercially available type associated with the selected adhesive used in connection with the cushion 105. The adhesive positioning strip may be mounted on the cushion in either a parallel or perpendicular fashion with regards to the longitudinal axis of the cushion. Further, the liner may be split so as to permit the removal of only a portion of the same exposing the adhesive incrementally; thus allowing continued use in opposing dental quadrants.

Conventional barrier bags, sometimes used with digital sensors, lack a suitable adhesive portion for securing the aforementioned positioning accessories and consequently must be used with more cumbersome basket holders which are typically less comfortable for the patient. Additionally, barrier bags fail to secure the sensor 110 in a desired position with respect to the positioning accessory 145, 165 and therefore are not able to insure that the sensor 110 remains in a desired position with respect to the positioning accessory 145, 165. The securing mechanism for aligning the sensor 110 with respect to the positioning accessory 145, 165 is provided by use of the integral adhesive positioning strip 150 in connection with the cushioning barrier 105 desirably facilitates the use of positioning accessories 145, 165 without directly attaching them to the sensor 110 itself. Thus, the comfort features and barrier qualities of the oral cushion 105 are not significantly impeded by the use of such accessories.

The oral cushion 105 may be desirably formed using a substantially seamless fabrication process wherein sharp, rough or generally uncomfortable protrusions in the oral cushion 105 are minimized to further improve the comfort features of the oral cushion 105. It will be appreciated that construction of the oral cushion 105 in this manner may be desirable to minimize surfaces that might potentially irritate tissue within the patient's oral cavity.

Furthermore, the oral cushion 105 may be constructed of a relatively thin material that does not significantly interfere with placement of the sensor 110 with respect to other oral alignment or positioning devices 145, 165. For example, as will be described in greater detail hereinbelow, the oral cushion 105 may be used in connection with a sensor basket, endodontic holder, or other sensor positioning accessory without appreciably impeding the ability of the sensor 110 to be secured, positioned, or oriented with respect to the positioning accessory.

In various embodiments, the oral cushion 105 may comprise a composite structure wherein a relatively thin material (e.g. plastic or polybag) is used in conjunction with foam or similar cushioning material positioned at strategic locations along the surface of the oral cushion 105 where contact with patient tissue may occur. For example, one or more of the edges or corners of the oral cushion 105 may be surrounded, contained, or overlaid by foam or similar cushioning material. In certain embodiments, a single edge, corner, or surface of the oral cushion 105 may comprise the foam or cushioning material composition, whereas in other embodiments, more than one edge, corner, or surface of the oral cushion 105 may comprise the foam or cushioning material composition. The positioning and size of the foam or cushioning material in relation to the oral cushion 105 may therefore be represented by numerous different constructions to accommodate various sizes and configurations of sensors 110.

FIGS. 7A–B illustrate another embodiment of a cushioning barrier 170 that incorporates a drawstring mechanism for providing containment of the sensor 110 within the oral cushion 105. In the illustrated embodiment, the sensor 110 is placed within the oral cushion 105 through the pocket opening 113 and secured in position via a drawstring closure 180. The drawstring closure 180 gathers the pocket opening 113 together such that the oral cushion 105 at least partially encloses the sensor 110 within the pocket 115. In a manner similar to the aforementioned embodiments, the generally sealed nature of the oral cushion 105 desirably protects the sensor 110 from contamination allowing it to be re-used from one patient to the next. Furthermore, foam or similar cushioning material 182 may be strategically located about the oral cushion 105 to confer a protective benefit as previously described.

In one aspect, the strings 185 of the drawstring closure 180 may be desirably configured to be of suitable length such that they extend out of the mouth of the patient. The relative length of the strings 185 may be such that they serve as an anti-aspiration or anti-swallowing safety device wherein the sensor 110 may be quickly removed from the patient's mouth by grasping the strings 185 and retracting the enclosed sensor 110. Alternatively, the strings 185 of the drawstring closure 180 may be desirably configured to be relatively short in length to minimize encumbrances due to the string presence. In various embodiments, the drawstring closure 180 provides a convenient and rapid way to securely enclose the sensor 110 without the use of adhesive material or tape. As with other previously described embodiments, the oral cushion 105 may desirably include an adhesive positioning strip 150 for purposes of joining to a support or positioning apparatus. In a further configuration, the strings 185 of the drawstring closure may be formed from a moisture resistant or moisture-retardant material to prevent undue accumulation of the patient's salvia or other liquids.

The oral cushion 105 may also comprise a generally soft sack or pouch (e.g. formed from foam or other suitable material) wherein the oral cushion 105 is sealed or closed at one end by gathering or collecting a portion of the sack with an elastic member in the general region illustrated by the drawstring closure 180 shown in FIG. 7B. The elastic member may be formed as an integral component of the oral cushion 105 wherein the opening 113 expands to accommodate insertion of the sensor 110 within the oral cushion 105 and subsequently contracts to thereby at least partially enclose the sensor 110 providing a convenient mechanism by which to protect the sensor 110. As with other embodiments, the oral cushion 105 may be formed with an adhesive positioning strip present on the surface of the oral cushion 105 to accommodate the use of various positioning and alignment devices.

Figure 8A:
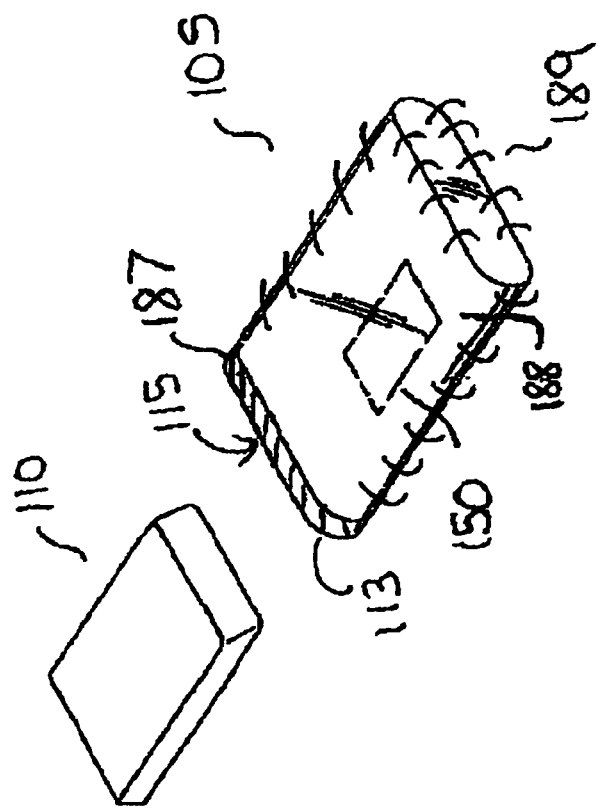
Figure 9:
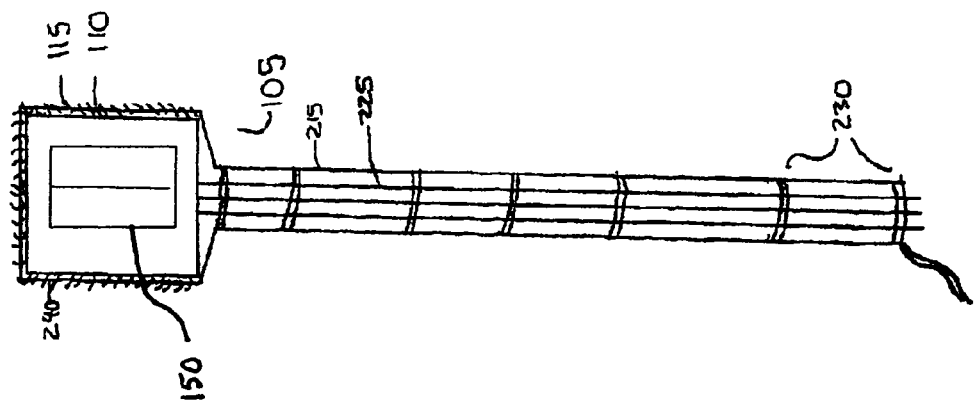
FIGS. 9A–D, illustrate other embodiments of an oral cushion formed as a combination polybag with foam or cushioning material surrounding the polybag on one or more sides.
Figure 9:
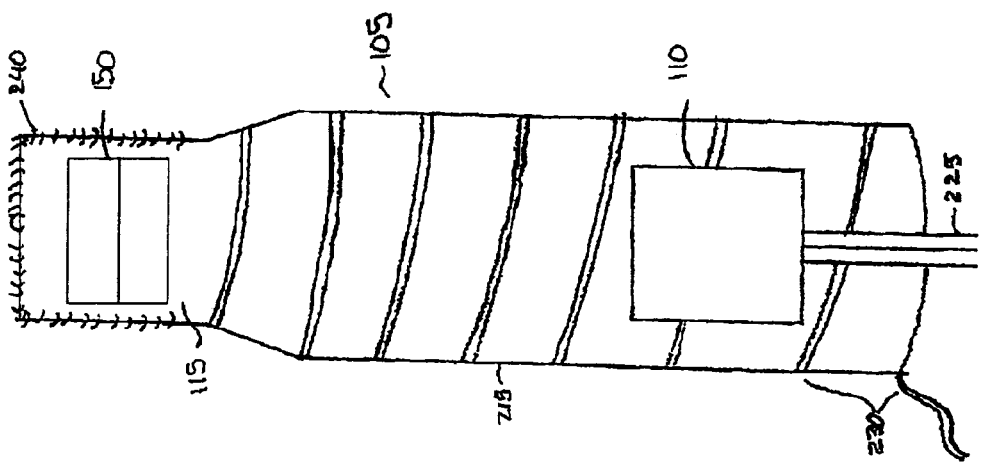
Figure 9C:
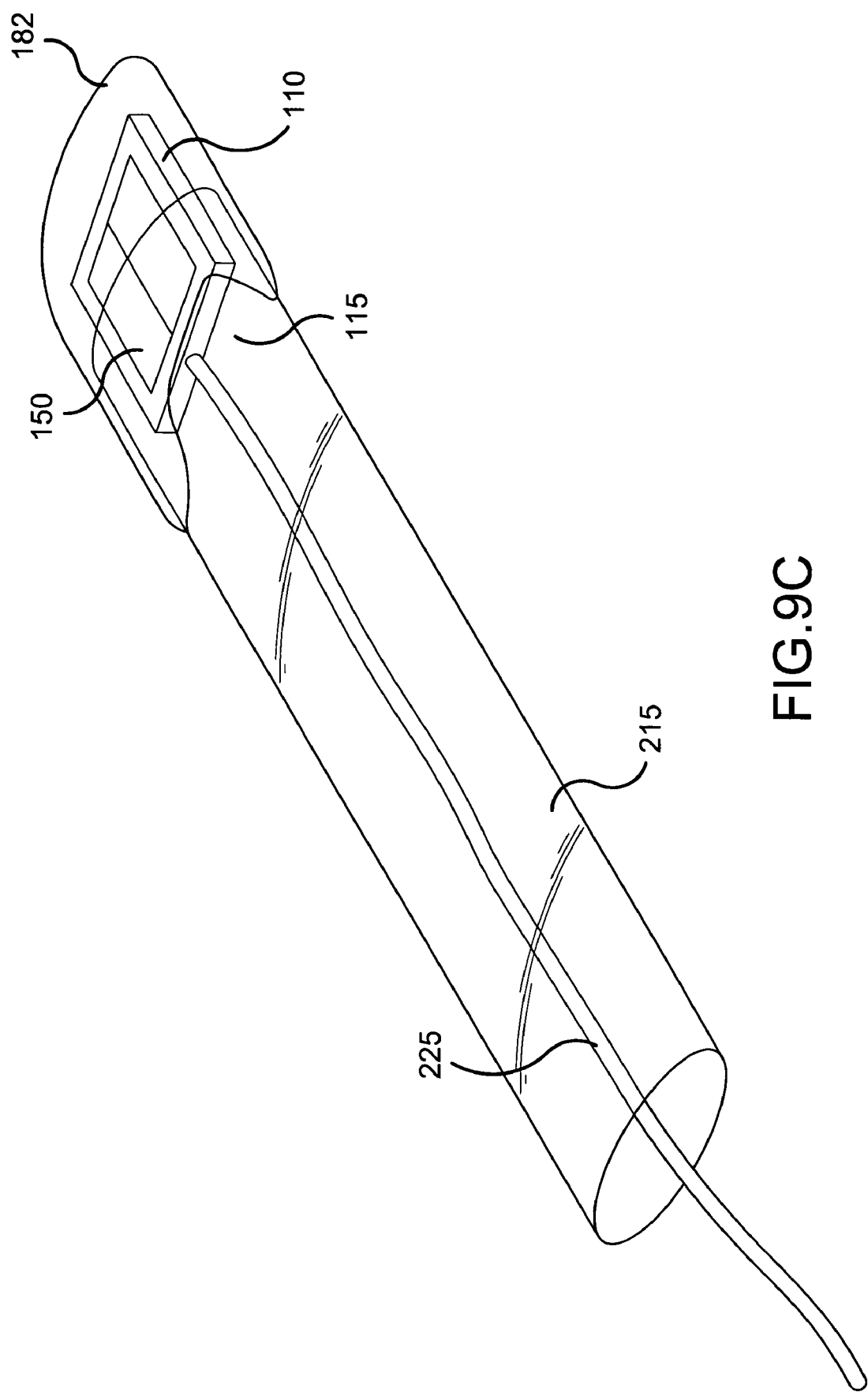
Figure 9D:
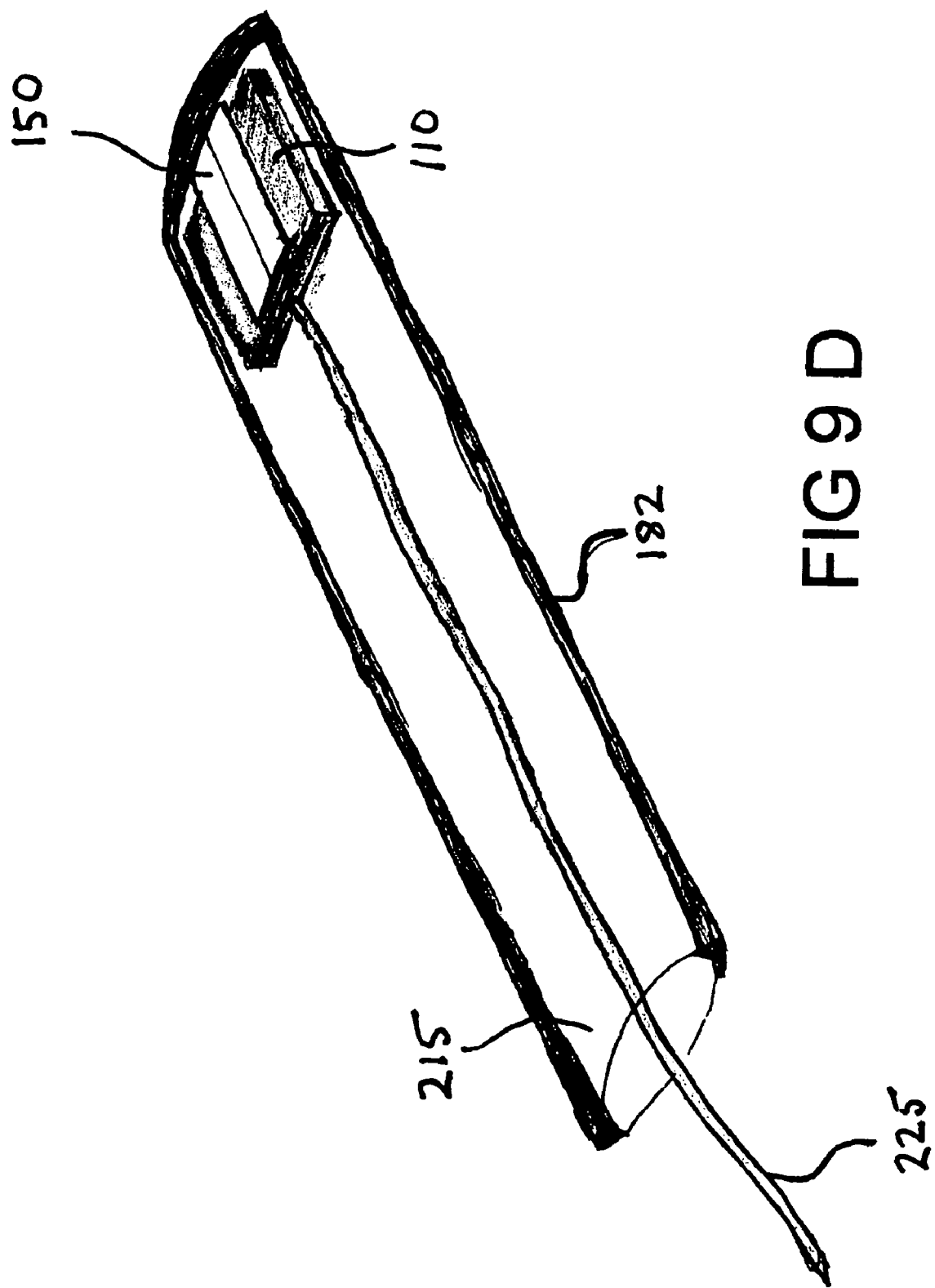

In further embodiments shown in FIGS. 8A and 8B, the oral cushion 105 may comprise a self-sealing covering having an adhesive portion 187 which secures the opening 113 of the pocket 115 once the sensor 110 has been inserted. In this configuration, the oral cushion 105 may comprise an inner member 188 (e.g. polybag or plastic material) having the adhesive portion 187 with an optional outer cushioning member 189 (e.g. foam or other generally soft material). The inner member 188 desirably provides a moisture resistant space to contain the sensor 110 keeping it generally dry and clean with the outer member 189 providing a comfortable cushion to prevent tissue abrasion.

As with other embodiments, the adhesive portion 187 may further comprise a removable liner or peel-off portion that covers and protects the adhesive component prior to use. In one aspect, the liner comprises a paper or plastic layer (possibly treated with an anti-stick coating) that may be easily removed from the adhesive portion 187 and prevents the cushion 105 from becoming sealed until desired.

Enclosure of the sensor 110 within the aforementioned embodiment of the cushion 105 may be accomplished by inserting the sensor 110 within the pocket 115, removing the adhesive liner (if present), and depressing, pinching, or folding over the general area about the opening closed. By this operation, contact between portions of the cushion 105 is made such that the adhesive portion 187 effectively seals the opening 113 thereby protecting the desired portions of the sensor 110.

Removal of the sensor 110 from the cushion 115 may be accomplished by pulling apart the region of the cushion 115 sealed by the adhesive and may further be facilitated by the use of a resealable or non-permanent adhesive. Additionally, the cushion 115 may be grasped at a desired location and torn or ripped to create an opening for the sensor 110 to be removed. The generally, inexpensive construction of the cushion 105 is such that it may be fabricated as a deposable product, however, the use of a resealable or non-permanent adhesive in connection with the opening 113 or positioning accessories 165 may allow for a reusable product. This embodiment may or may not include a non-permeable barrier liner. It may be used alone or in conjunction with a sensor previously placed in a barrier sheaf. The benefit of this embodiment is the cushioning effect and ease of positioning due to the employment of the positioning strip used to secure positioning apparatus or a bite tab 145.

FIGS. 9A–D illustrate other embodiments of the oral cushion 105 formed as a combination sack or bag (e.g. thin plastic polybag) with foam or cushioning material surrounding the sack on one or more sides 182. In one aspect, the oral cushion 105 comprises the pocket section 115 joined with an elongated section 215. The sensor 110 is desirably inserted into the elongated section 215 and pushed through until it resides within the pocket section 115. As with other embodiments, the sensor 110 may be of a wireless type or a wired type as illustrated. In this particular implementation, the wires 225 of the sensor 110 may be desirably shielded from contamination along with the sensor 110 by the elongated section 215.

In certain embodiments, the oral cushion 105 comprises a drawstring enclosing mechanism 230 used to seal the sensor 110 and wires 225 within at least a portion of the oral cushion 105. The drawstring enclosing mechanism 230 may be formed as a vertical, horizontal or spiral drawstring which is attached to the oral cushion 105 at various positions. When the drawstring 236 is engaged the oral cushion 105 collapses about the sensor 110 and wires 225 thereby collecting any excess material relatively closely about the sensor 110 and wires 225 to effectively protect them from contamination and debris. As with other embodiments, the adhesive positioning strip 150 may be utilized to enable the oral cushion 105 to be joined with a bite tab 145, bite plate, holder, or other component to which the sensor 220 may be desirably affixed. It will be appreciated that the drawstring enclosing mechanism 230, illustrated in FIGS. 9A–B, may be omitted in certain embodiments or alternatively the drawstring may be implemented as an anti-aspiration device without necessarily providing the sealing functionality described above.

In certain embodiments, the construction of the oral cushion 105 may be accomplished by hot stamp methods or the like in which the sides of the oral cushion 105 are joined to form the enclosable space within which the sensor 110 resides. Additionally, the oral cushion 105 may be formed in part or whole from thin plastic, foam, or a combination of materials to provide generally soft surfaces 240 with little or no rough or sharp edges about the regions of the oral cushion 105 that may engage with the mouth or tissue contained therein. For example, the construction of the oral cushion 105 may comprise a combination of materials wherein the pocket section 115 is formed from a selected material such as foam and the elongated section 215 is formed from another material such as plastic or polybag material. All embodiments may or may not include adhesive positioning strips 150 located on the exterior, so placed to ease the attachment/detachment of various holding devices. All embodiments may or may not include a bite tab which the patient would bite on or occlude, to hold the sensor or film and oral cushion in place.

FIG. 10 illustrates an exemplary configuration of the oral cushion 105. In this configuration, the seamed or seamless elongated polybag tubing 215 is joined to the cushion 105 by any of various methods. On the external face of the cushion, an adhesive positioning strip 150 may be applied either perpendicular or parallel with the longitudinal axis of the device. The adhesive positioning strip may be divided in portions in such a manner as to permit the removal of one or more strips of protective liner in order to expose the adhesive incrementally, thus permitting the adhesion to various positioning devices. The technician simply slips the sensor 110, which may be equipped with a wire 225 or be wireless, into the opening 113, then slides the sensor forward into the cushion 105. The liner covering the adhesive positioning strip may then be removed to attach the cushion to a positioning device. After use, the sensor is removed and the device is discarded. The elongated nature of the device permits the shielding from saliva and various other debris from the oral cavity from contact, therefore maintaining sterility while providing comfort to the patient during the x-ray process.

Figure 11A:
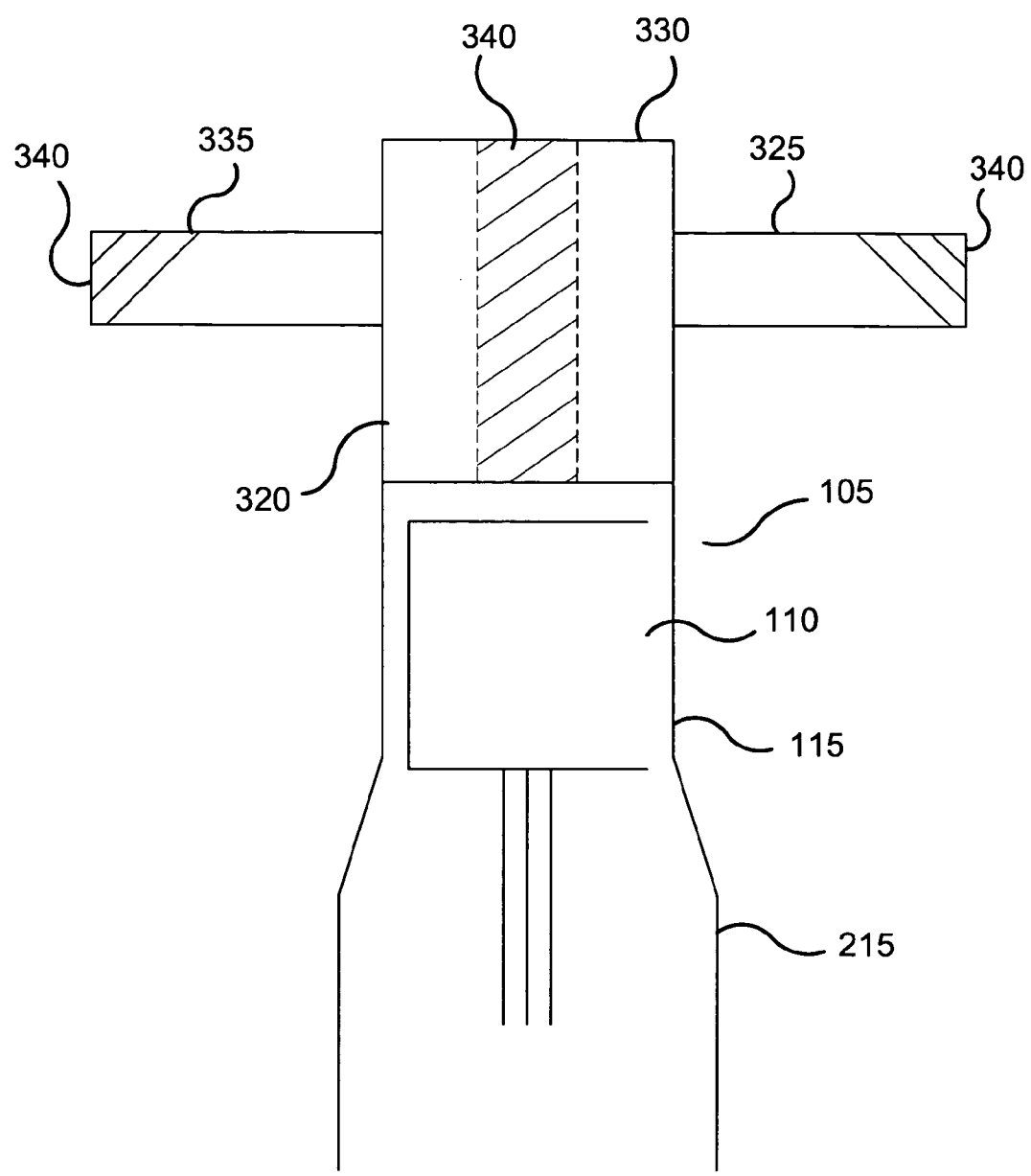

FIG. 11A illustrates another configuration of oral cushion 105 to be used in conjunction with a bite plate, carrier basket, or other device upon which or within which the sensor 110 is to be attached. In one aspect, the oral cushion 105 comprises the pocket section 115 and optionally the elongated section 215 similar to that described in FIGS. 9–10. The sensor 110 is desirably inserted into the pocket section 115 and sealed in any of various different manners exemplified in previous figures.

In this configuration of the oral cushion 105, a padded section 320 extends from the pocket section 115 for purposes of cushioning a bite plate, carrier basket, or other device to which the sensor 110 is attached. The padded section 320 may comprise one or more subsections 325–335 that may be folded about the portions of the bite plate, carrier basket, holder, etc. that engage with the tissue of the oral region. Providing the padded section 320 therefore provides a mechanism to cover or pad various portions of the external apparatus to which the sensor 110 is to be contained or secured. In various embodiments, the padded section 320 may include an adhesive backing 340 that may be used to secure the various subsections 325–335 of the padded section 320. The oral cushion 105 of this configuration therefore desirably protects and pads the sensor 110 and also pads various other components which may engage with the patient's tissue. Further illustration and description of the placement and use of the oral cushion 105 is shown in connection with FIGS. 11B–12.

FIG. 11B depicts another configuration of the oral cushion 105 used alone or in conjunction with a separate polybag tube 215 barrier shield. In this configuration, the oral cushion is a flat, thin piece of foam, plastic, rubber or other soft material that is coated on one side either partially or completely with an adhesive, 340. The technician places the sensor 110 which may or may not be wireless, into the polybag tube or other barrier sheath. After removing the liner from the oral cushion, exposing the adhesive, the sensor within the polybag tube is placed on the oral cushion. Either side is folded to the middle, completely enclosing the sensor. The adhesive positioning strip 150 may or may not be placed on either side of the closed flaps as well as on the back of the oral cushion for use in attaching the oral cushion to various positioning devices such as bite tabs 145. An additional variant on this embodiment may or may not include the polybag or barrier sheath pre-attached to the oral cushion.

Figure 12:
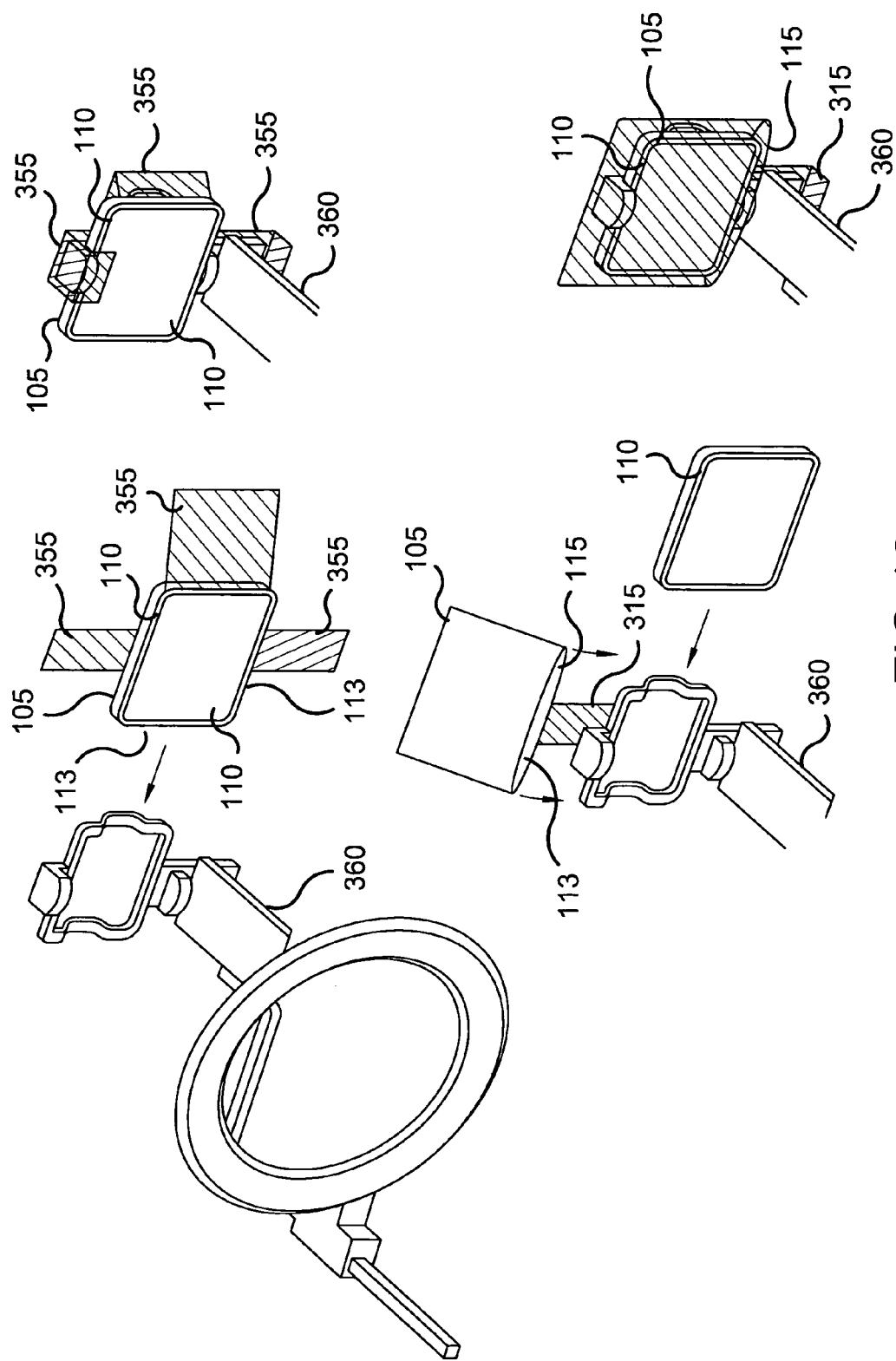
FIG. 12 illustrates another configuration of an oral cushion which covers at least a portion of the sensor and the sensor within the oral cushion.

FIG. 12 illustrates still another configuration of the oral cushion 105 having foldable tab sections 355 that may be desirably used to cover rough, sharp, or otherwise potentially uncomfortable sections of a bite plate, holder, or other device 360 used in connection with the sensor 110 such that discomfort felt from these sections when in use by the patient are reduced or minimized. In one aspect, the oral cushion 105 is constructed to allow the sensor 110 to be inserted into the bite plate, holder or other device 360 without significant impediment. The foldable tab sections 355 may then be positioned in a manner that allows them to be folded over various portions of the bite plate, holder or other device 360. As previously noted, an adhesive layer 340 may be used in connection with the tab sections 355 to facilitate securing them in position providing an additional safety measure in preventing accidental aspiration.

In an alternative embodiment, the oral cushion 105, comprising a pocket section 115 with an opening 113 on either side and, optionally an elongated section 315 may be slipped over the sensor 110 when positioned within the bite plate, holder or other device 360. When so positioned, the pocket section 115 may be used to enclose the sensor 110 and at least a portion of the bite plate, holder or other device 360 and the elongated section 315 may be used to cover other portions of the bite plate, holder, or other device 360 that may contain exposed edges, corners, or protrusions that may cause the patient discomfort. In certain embodiments, the oral cushion 105 may further include one or more slits that facilitate positioning the oral cushion over various sensor holders.

FIGS. 13A–B illustrates other configurations of an oral cushion 105. In one aspect, the oral cushion 105 comprises a foam or poly bag with foam 405 present about one or more sides 407 that are generally closed or sealed. In one preferred embodiment, the foam 405 surrounds three sides of the oral cushion 105 and the remaining side 415 is open to receive the sensor 110 in the pocket 115. From the open side 415, the oral cushion 105 may be slipped over a sensor 110 and at least a portion of a holder, basket, bite plate, etc to which the sensor 110 is attached or secured.

A comfort strip or portion of padding material 425 may further extend from a portion of the oral cushion 105 having an adhesive portion used for securing the oral cushion 105 to a sensor positioning accessory comprising for example a sensor basket, endodontic holder, bite tab, or sensor positioning arm. Such a configuration of oral cushion 105 may desirably be used in connection with conventional barrier bags to improve the comfort of the patient when the sensor and holder are placed within the patient's mouth. In one aspect, the adhesive portion of the comfort strip facilitates positioning of the cushioning projection about one or more contours associated with the sensor positioning accessory and acts as an additional safety measure to prevent the patient from accidentally aspirating the oral cushion 105. Any embodiment that does not have the comfort strip 425 will be equipped with an adhesive safety strip 150 in order to secure the oral cushion to the positioning device and therefore prevent accidental aspiration while supporting positioning. (see FIG. 15A–B) As with other embodiments, a generally soft padding material 405 may surround various portions of the oral cushion 105 to further improve patient comfort.

While, certain aforementioned embodiments have described the oral cushion 105 for use with various positioning devices and accessories 165, 360 it will be appreciated that the oral cushion may additionally be used without the positioning devices and accessories 165, 360. For example, in certain instances or modes of dental imaging, placement of the sensor 110 within the oral cavity does not necessarily require use of the positioning devices 165, 360 and can be accomplished either by the patient positioning and retaining the sensor 110 manually or by placement of the sensor 110 without the need for external retention during imaging. The ability to selectively utilize the adhesive portion 150 as necessary or desired improves the flexibility of the oral cushion to accommodate various different imaging circumstances or situations using a singular cushion configuration.

Figure 14B:
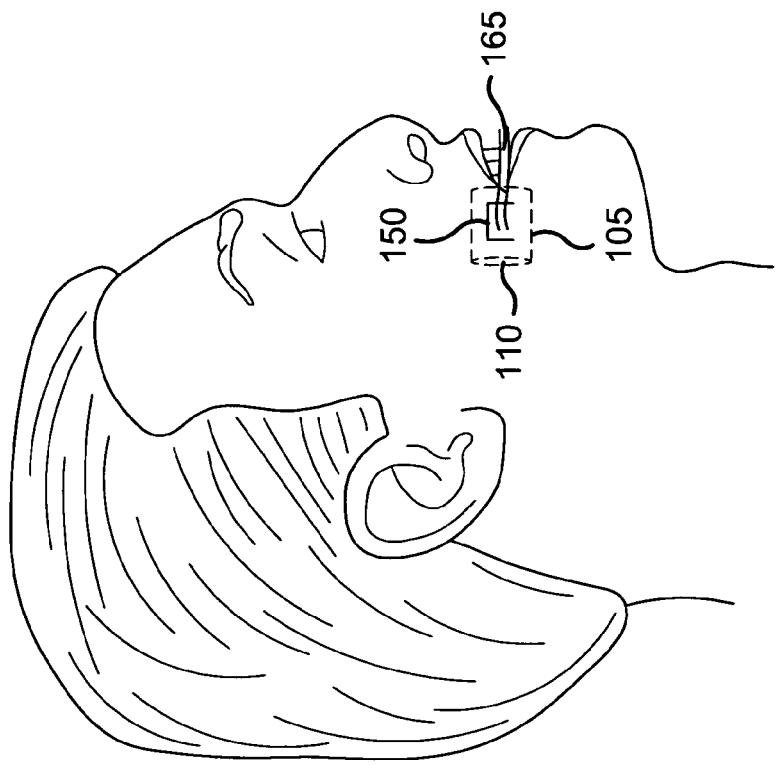
FIGS. 14A–B illustrates the use of the oral cushion in connection with the sensor and positioning accessory when placed within the oral cavity of a patient.
Figure 14A:
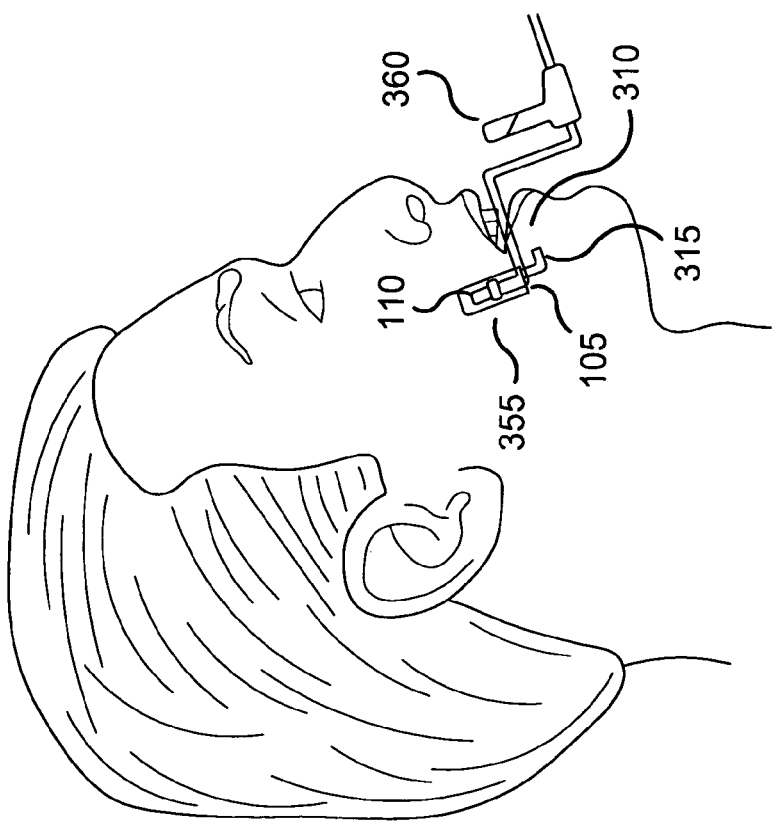

FIGS. 14A and 14B illustrate examples of the placement of the dental sensor 110 protected by the cushion 105 with various positioning accessories 165, 360 within the oral cavity. Use of the oral cushion 105 in connection with the dental sensor 110 desirably allows positioning and alignment of the dental sensor 110 in much the same way as is done without the cushion 105 being present. For example, as shown in FIG. 14A, the dental sensor 110 is secured to the positioning accessory 360 and is protected by the cushion 105 as previously described in FIG. 12. In one embodiment, foldable tab sections 355 may be used to cover various portions of the positioning accessory 360 that might come into contact with the patient's oral tissues. Alternatively the oral cushion 105 may comprise the aforementioned elongated section 315 that may be positioned in such a way as to substantially prevent contact between a portion of the positioning accessory 360 and the patient's oral cavity. When inserted into the patient's mouth, a portion 510 of the oral cushion 105 may extend along the positioning accessory 360 such that this portion 510 is intended to be bit down upon by the patient. The relatively soft construction of this portion 510 of the cushion further improves patient comfort during the imaging process.

In one mode of operation, use of the oral cushion 105 in connection with the dental sensor 110 and positioning accessory 165, 360 results in the positioning of the dental sensor 110 generally behind and adjacent to a desired portion of the patient's teeth. Specific alignment of the dental sensor 110 is based upon the type of image to be taken or the portion of the patient's teeth to be imaged. The generally resilient nature of the oral cushion 105 is such that it may be used for a protracted period of time wherein multiple images are acquired without significant concern over the breakdown of the barrier between the patient's tissue and the dental sensor. Additionally, the comfort provided by the oral cushion 105 allows more images to be taken or more care and time to be put into aligning the dental sensor 110 without causing the patient undo pain or discomfort during the imaging process.

As will be appreciated by one of skill in the art, application of the oral cushion 105 to the dental sensor 110 desirably protects that dental sensor 110 from contact with the patient's saliva as shown in FIG. 14A–B. Furthermore, the oral cushion 105 protects the patient from direct contact with the dental sensor 110 and various portions of the positioning accessory 165, 360 thus reducing the likelihood of tissue injury and patient discomfort during the imaging process.

FIG. 14B further illustrates the use of the oral cushion 105 in connection with a dental sensor 110 and positioning accessory 165 comprising a bite plate. As described above in connection with FIG. 14A the dental sensor is substantially protected from contact with a patient's oral tissue and vice versa. Additionally, the location of the adhesive portion 150 of the oral cushion 105 is such that it aids in the proper alignment of the positioning accessory 165 with respect to the dental sensor 110 and further facilitates alignment of the dental sensor 110 within the patient's oral cavity when the positioning accessory 165 is bit down upon.

Figure 16:
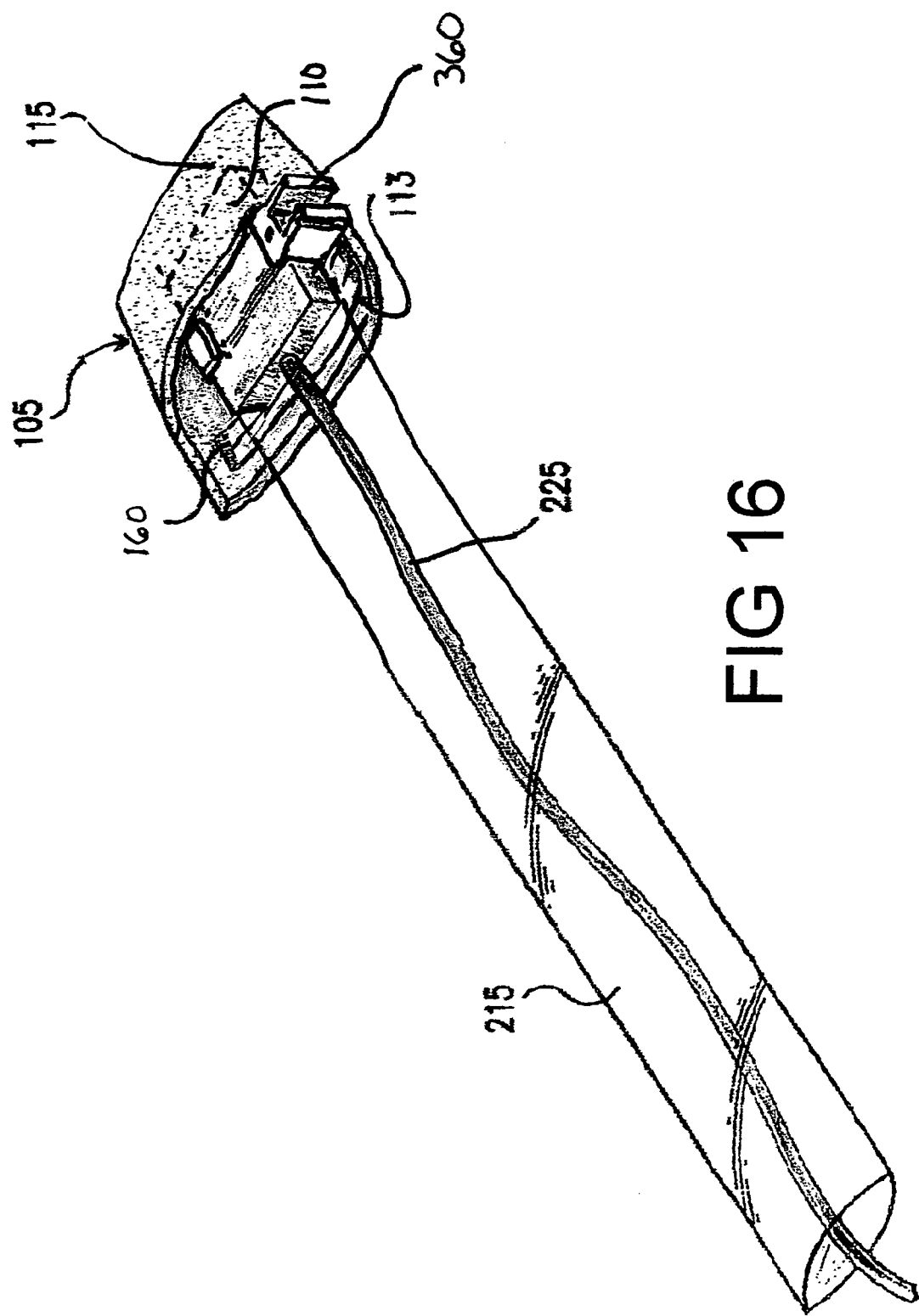

FIGS. 15 and 16 illustrate an embodiment of the oral cushion 105 formed of material that is gentle or soft to a patient's mouth, such as plastic, foam or cushioning material, having a front and a back side with a pocket section 115 disposed there between, the pocket section 115 generally conforming to the shape and dimensions of the sensor 110 with an opening 113 into which the sensor may be positioned within the pocket 115. An adhesive safety strip 160 is disposed along at least a portion of the oral cushion 105. This adhesive safety strip is critical to preventing the accidental aspiration of the oral cushion. After the technician places the sensor 110 into the elongated polybag tube 215, and thence into a holding device or basket 360, the protective paper or covering is removed from the adhesive safety strip 160, exposing the adhesive. The entire sensor with holding device 360 attached may be placed into the oral cushion pocket 115, and held in place by the adhesive safety strip 160. FIG. 15 shows an exploded view of the device with the individual portions revealed, while FIG. 16 shows the device fully inserted into the oral cushion 105 as prepared for insertion into the mouth of a patient. The elongated section 215 is generally made out of plastic or polybag material, but can be made of any softer material, such as plastic or foam, that is suitable to secure the wire 115 and be comfortable to the touch of a patient. Plastic material is suitable for the elongated section 215 because after the sensor 110 and wire 225 are inserted, the elongated section (manufactured of suitable plastic) can be pressed and compressed upon itself to reduce the size of material to be inserted into the patient's mouth.

The front and back side of the oral cushion 105 may be sealed or folded together on one or more sides while one side may be left open or unsealed. An adhesive safety strip 160 may be placed on the front, inside and/or back portions of the oral cushion 105 to secure the position of the sensor 110 within the oral cushion 105 and to secure the cushion 105 within a positioning accessory 165, 360. By inside portion of the oral cushion 105, it is meant the interior portions of the pocket section 115. FIG. 15 shows the adhesive safety strip positioned on the front, inside portion of oral cushion 105 and as a single adhesive safety strip. An additional embodiment where the adhesive safety strip 160 is divided into multiple (such as two) sections that can be individually exposed with removal of a removable liner or peel-off portion that covers and protects the adhesive strip component prior to use is also clearly envisioned. It will, therefore, be appreciated the device of the invention includes various embodiments wherein the adhesive safety strip 160 can be in one or multiple sections and can be positioned on the front and/or back of the oral cushion 105, depending upon the desires of the practitioner using the device.

In order to aid in easy placement of sensor 110, the front and back sides of the oral cushion 105 may be of the same or different lengths. If equal or approximately equal lengths of material are used to form the front and back sides of the oral cushion 105, a slit may be made approximately half way up one or both sides of the oral cushion 105 to accommodate the sensor 110. In the embodiment shown in FIGS. 15 and 16, one side of the oral cushion 105 is larger (longer) than the other side of the oral cushion. However, the front and backsides of the oral cushion 105 may be fashioned in varying lengths to -accommodate the many sizes of x-ray film and dental sensors. Either side may or may not include an adhesive positioning strip or bite tab.

The sensor 110 is desirably inserted into the elongated section 215 and pushed through until it resides within the pocket section 115. As with other embodiments, the sensor 110 may be of a wireless type or a wired type as illustrated. In this particular implementation, saliva, germs and other oral contaminants are prevented from directly contacting the wires 225 of the sensor 110 or the sensor 110 itself by the elongated section 215.

Figure 17:
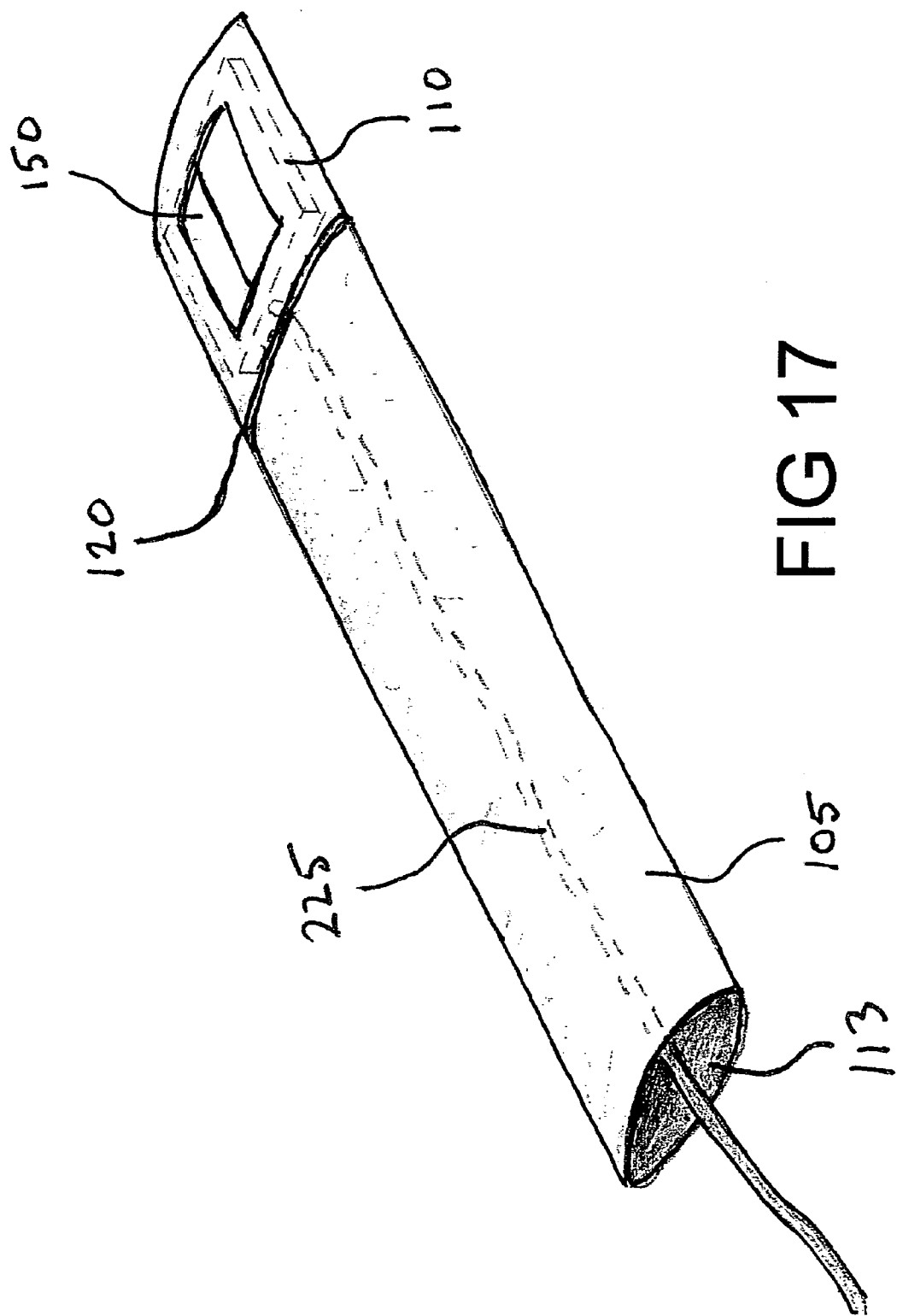
FIG. 17 illustrates a further embodiment of an oral cushion that incorporates an elongated section constructed entirely of foam, soft rubber or plastic tube designed to receive and contain a wired or wireless sensor.

FIG. 17 represents another embodiment of the oral cushion 105. In this embodiment, the entire body of the oral cushion 105, to include the elongated portion, is made from a soft foam, plastic or rubber material that fully encloses the sensor 110 on three sides in a tube. In order to ease alignment of the sensor 110, a sensor alignment line is provided on the oral cushion 105. An adhesive positioning strip, 150, is provided on one or more sides, positioned perpendicular or parallel to the longitudinal axis of the oral cushion, 105, in order to ease the attachment of various positioning devices.

While use of the oral cushion 105 in connection with the dental sensor 110 and positioning accessory 165 is shown in two modes, it will be appreciated that other operational modes exist and thus the use of the oral cushion 105 should not be construed to be limited to those illustrated. Additionally, various embodiments of the oral cushion 105 have been described and illustrated that may be used in connection with a variety of different dental sensor 110 and positioning accessory configurations. As such, each of these combinations is conceived to be but other embodiments of the present teachings.

Although the foregoing description of the present teachings has shown, described and pointed out novel features of the invention, it will be understood that various omissions, substitutions, and changes in the form of the detail of the apparatus as illustrated, as well as the uses thereof, may be made by those skilled in the art without departing from the spirit of the present invention. Consequently the scope of the present teachings should not be limited to the foregoing discussion but should be defined by the Claims.

What is claimed is:

1. An intra-oral dental comfort device capable of being configured for use with or without a positioning accessory, the device comprising:
    an oral cushion having first and second sides with a pocket disposed therebetween, the pocket dimensioned to receive and maintain a dental sensor in a generally secure position within the oral cushion, the oral cushion further configured to provide a comfort barrier between at least a portion of the dental sensor and tissue in a patient's oral cavity;
    an adhesive safety strip disposed along at least a portion of the oral cushion to secure an elongated section to the oral cushion wherein said elongated section is designed to receive a dental sensor or film; and
    an adhesive positioning strip disposed along at least a portion of the oral cushion, the adherent member configured to receive and secure the positioning accessory to the oral cushion such that the dental sensor may be positioned in a desired orientation within the patient's oral cavity allowing imaging of at least a portion of the patient's teeth by an imaging device used in connection with the dental sensor.

2. The intra-oral dental comfort device of claim 1, wherein the dental sensor consists of a digital x-ray sensor or an x-ray film packet.

3. The intra-oral dental comfort device of claim 2 wherein, the oral cushion is configured to accommodate wireless or wired digital x-ray sensors or film.

4. The intra-oral dental comfort device of claim 1, wherein the oral cushion is formed from a soft or malleable material generally resistive to tissue abrasion.

5. The intra-oral dental comfort device of claim 4, wherein the oral cushion composition comprises foam, plastic, rubber, or paper.

6. The intra-oral dental comfort device of claim 1 wherein, the positioning accessory comprises a bite plate, a bite tab, an endodontic tab, an anterior periapical tab, a bitewing tab, a posterior periapical holder, a sensor basket, an endodontic holder, film positioning device, or a sensor positioning arm used for positioning the dental sensor within the patient's oral cavity.

7. The intra-oral dental comfort device of claim 1 wherein, the adhesive positioning strip comprises an adhesive component that allows the positioning accessory to be removably secured to the oral cushion or permanently attached and disposed of with a positioning device.

8. The intra-oral dental comfort device of claim 1, wherein the elongated section is formed from a plastic or polybag material.

9. The intra-oral dental comfort device of claim 1 wherein the oral cushion is sized to accommodate an oral sensor contained within a sensor sheath or sensor holder.

10. The intra-oral dental comfort device of claim 1 wherein, the oral cushion is formed so as to lack sharp or rough seams that might otherwise abrade portions of the patient's oral cavity.

11. The intra-oral dental comfort device of claim 1, wherein at least two of the edges formed by the first and second sides of the oral cushion are sealed.

12. The intra-oral dental comfort device of claim 1, wherein the first and second sides of the oral cushion are of equal or different length.

13. The intra-oral dental comfort device of claim 4, wherein the material is colored, clear, opaque, scented, unscented, flavored or unflavored.

14. The intra-oral dental comfort device of claim 1, wherein said adhesive positioning strip comprises one or more removable liner portions to cover the adhesive when not in use, said liner portions being indirectly removable to permit exposure of the adhesive.

15. The intra-oral dental comfort device of claim 8, wherein the edges of said elongated section are formed of or covered with foam to avoid tissue abrasion.

* * * * *